United States Patent [19]

Cohen

[11] Patent Number: 4,543,063

[45] Date of Patent: Sep. 24, 1985

[54] ELASTOMERIC IMPRESSION MATERIAL FOR TOOTH AND SUPPORTING STRUCTURE DUPLICATION

[76] Inventor: Howard Cohen, 2791 W. 5th St., Brooklyn, N.Y.

[21] Appl. No.: 644,731

[22] Filed: Aug. 27, 1984

Related U.S. Application Data

[62] Division of Ser. No. 346,570, Feb. 8, 1982, Pat. No. 4,468,202.

[51] Int. Cl.$^4$ .......................... A61C 8/00; A61C 13/00
[52] U.S. Cl. ................................. 433/175; 433/199.1; 433/201.1; 433/215; 433/168.1
[58] Field of Search .............. 433/201, 199, 215, 173, 433/194, 175, 176

[56] References Cited

U.S. PATENT DOCUMENTS 3,919,773 11/1975 Freeman ............................. 433/175
4,491,453 1/1985 Koblitz ................................ 433/201

*Primary Examiner*—Robert Peshock
*Attorney, Agent, or Firm*—Robert W. Fiddler

[57] ABSTRACT

A material and method are disclosed facilitating the forming of impressions of teeth and/or supporting structures, such as the alveolar ridge to be duplicated and restored. An elastomeric impression material, preferably subject to photochemical or chemical curing, is provided, such for example as formed from polyesters, polyethers, polysulfides, silicones, and ethylene imines, or derivatives thereof, containing a filler material, such as talc, calcium carbonate, colloidal silica, glass, quartz, acrylates, etc., and impregnated with a hemostatic agent such as a vasoconstrictor or astringent or the like with the impression material serving to maintain subgingival tissue in a retracted condition without bleeding, so as to permit an impression to be taken of a tooth surface area and volume extending below the gumline, without requiring use of gum retracting cords or bands. In use, a portion of the impression material in a cord, ring or rhomboid shape, or the like, is wedged between the gum and the tooth to conform to the contour of the tooth below the gum and cured by chemical or photochemical means. This procedure is followed by the taking of an impression material adhering to the impression material below the gum, thereby providing an exact duplication of the tooth, both above and below the gum. The impression materials may be color-coded to delineate soft from hard tissue. By making the impression material photochemically or chemically curable the time for the procedure may be controlled, and the dentist may reline dentures without the need for laboratory work, and use it in other ways not limiting it to those mentioned.

2 Claims, No Drawings

ELASTOMERIC IMPRESSION MATERIAL FOR TOOTH AND SUPPORTING STRUCTURE DUPLICATION

This application is a division of application Ser. No. 346,570 filed Feb. 8, 1982, now U.S. Pat. No. 4,468,202.

BACKGROUND OF THE INVENTION

This invention relates to the art of dental duplication, and more particularly to means including a method and material facilitating the forming of impressions of teeth and/or supporting structures, such as the alveolar ridge to be duplicated and/or restored, with the resulting impressions providing both a sub and supra gingival contour of the tooth to be duplicated and/or restored.

In the duplication and/or restoration of teeth, an impression is taken of the tooth to be restored, with the impression subsequently employed as a mold to form a desired replacement and/or restoration, such for example as crowns, jackets, bridges, implants, plate relining and the like. In forming this desired impression, it is desired to obtain both a supra and sub gingival impression of the tooth, that is, an impression of the tooth showing tooth surface contours both above and beneath the gum line.

Supra-gingival or above gum line impressions are taken by merely applying the impression material to the tooth to be replaced and/or restored. Contours of the sub gingival tooth surface require that the gum be retracted so as to expose this tooth area. In the past, this has entailed the utilization of so-called retraction cords or elastic bands, which have generally been impregnated with astringents or the like vasoconstrictors, serving to restrict bleeding of the gingival tissue being retracted.

As is apparent, the positioning of the retracting cords and/or elastic bands, and the subsequent application of the impression material involves careful manipulations, increasing the time required, possibility of error, and resulting costs.

BRIEF DESCRIPTION OF THE INVENTION

It is with the above considerations in mind, that the present, improved impression forming means, including both material and method have been evolved, serving to facilitate the formation of dental impressions, without necessitating the use of separate gum retracting cords or bands, minimizing manipulation requirements and the possibility of error.

Accordingly, among the primary objects of the invention is the provision of dental impression means, including both material and method implementing the formation of a sub-gingival impression without requiring the use of gum retracting cords or bands.

Another object of the invention is to provide means for forming a supra and sub-gingival impression with the surfaces of the impression above and below the gum line clearly delineated.

Another object of the invention is to provide means facilitating the formation of tooth impression with a minimum of manipulation and maximum speed.

It is also an object of the invention to provide means for making a dental impression permitting the dentist to control time of procedure.

A further object of the invention is to provide means permitting relining of dentures in or out of the mouth of the patient.

Another object of the invention is to provide means for obtaining a sub-gingival seal for jackets or crowns.

A further object of the invention is to provide an improved packaging for impression material facilitating its use.

An additional object is to provide improved impression material.

These and other objects of the invention, which will become hereafter more apparent, are achieved by forming an impression material of an elastomer, which may be a photochemically or chemically cured material, containing a filler providing desired density and may be impregnated with a hemostatic agent such as vasoconstrictor, astringent, and the like, serving to minimize bleeding. In accordance with one embodiment of the invention, a package for the impression material is provided, having a plurality of individually squeezable manually compressable compartments, each preferably having a self-sealing dispensing outlet.

Alternatively, the impression material may be formed as an elongate strand adapted to be withdrawn from a container and wound over the tooth surface, or may be ring or rhomboid shaped.

In taking tooth impressions, the gums of the patient are displaced by use of a tool and the elastomer is applied to the tooth surface above and below the gum line by dispensing the elastomer from the package.

A feature of the invention resides in the provision of an elastomeric impression material that can be molded to the underlying structures, such as the alveolar ridge and thereafter photochemically cured.

Another feature resides in the fact that the material may be used in the construction of a prosthesis or as an implant, and thereafter photochemically cured.

An additional feature resides in the provision of means for relining a denture at chairside by use of photochemically cured impression material.

DESCRIPTION OF PREFERRED EMBODIMENT

The invention is practiced by utilizing a relatively high density elastomeric material, which is preferably photochemically curable, but may also be chemically cured, impregnated with a hemostatic agent. The following formulations have been found suitable for photochemically curing.

EXAMPLE 1

100 gm of a polyethylene glycol with a molecular weight in the range of 500 to 20,000 is heated with 12 gm of crotonic anhydride for one hour at 150° C. and 1 hour at 180° C. Volatile ingredients are removed by vacuum at 180° C. or some similar means. The substance is of a wax like consistency at room temperature. Benzoin alkyl ether in the range of 0.05% to 1% (based upon weight of product) is mixed with the polyether product and subjected to ultraviolet light in the region of 365 nanometers. The mixture is transformed into a transparent rubber-like mass.

EXAMPLE 2

The resin prepared in Example 1 was mixed with camphoroquinone in the range of 0.05% to 1% and N,N dimethylamino-ethyl methacrylate in the range of 0.05% to 1% based on the weight of the resin. When the mixture is exposed to visable light in the range of 400°–450° nm a transparent rubber-elastic mass is formed.

EXAMPLE 3

The resin as in Example 1 is mixed with benzoyl peroxide in the range of 0.05% to 0.5% and 0.05% to 0.5% dimethylaniline and allowed to cure at ambient temperature.

EXAMPLE 4

100 gm of a polyethylene glycol with a molecular weight in the range of 500 to 20,000 is heated with 12 gms of methacrylic anhydride for one hour at 150° C. and one hour at 180° C. Volatile ingredients are removed by vacuum or some other suitable means. Benzoin alkylether in the range of 0.05% to 1% (based on weight of product) is mixed into the product and the mixture exposed to ultraviolet light in the region of 365 nm. The mixture is transformed into a rubber-elastic mass.

EXAMPLE 5

Add camphoroquinone in the range of 0.05% to 1% and N,N dimethylamino ethyl methacrylate in the range of 0.05% to 1% to the product of Example 4. When the mixture is exposed to visible light in the region of 400–450 nm, a rubber-like mass is formed.

EXAMPLE 6

250 g. of a polyester with terminal OH groups and a mean molecular weight in the range of 500 to 20,000 made from adipic acid with addition of 101 mol percent sebacic acid and triethylene glycol, with addition of 10 mol percent of hexane diol-1,6 are heated under nitrogen with 21 g. crotonic anhydride for one hour to 150° C., and for two hours to 180° C. Subsequently, the crotonic acid formed and excessive crotonic anhydride are removed by a vigorous current of $N_2$ at 200° C. Mix product with benzoin alkylether in the range of 0.05% to 1% and expose to ultraviolet light in the region of 365 nm wave length gives a rubbery product.

EXAMPLE 7

Mix product of Example 6 with camphoroquinone in the range of 0.05% to 1% and N,N-dimethylamino ethyl methacrylate in the range of 0.05% to 1% and cure with visible light in the region of 400–450 nm.

EXAMPLE 8

Substitute methacrylic anhydride for crotonic anhydride to get product. Add benzoin alkylether and expose to ultraviolet light in the region of 365 nm.

EXAMPLE 9

Mix product of Example 8 with camphoroquinone in the range of 0.05% to 1% and N,N dimethylamino ethyl methacrylate in the range of 0.05% to 1% and expose to visible light in the region of 400–450 nm.

EXAMPLE 10

720 g. of a polyester prepared from adipic acid with addition of 15 mol percent pimelic acid and triethylene glycol which substantially contains terminal OH-groups and has a mean molecular weight in the range of 500 to 20,000, are heated with 230 g. crotonic anhydride for one hour to 150° C. and for one hour to 200° C. Subsequently, excess crotonic anhydride is blown off at 200° C.

EXAMPLE 11

50 g. of a branched polyester prepared from adipic and sebacic acids, trimethylolethane and triethylene glycol, in a molar ratio 9:1:0.67:11, which has a viscosity of 140 poises/25° C., are heated with 15.6 g. crotonic anhydride for one hour to 150° C. and one hour to 200° C. Subsequently, the volatile portions are blown out with $CO_2$ at 210° C.

EXAMPLE 12

82 g. of a polyester made from adipic acid, sebacic acid, trimethylol propane and triethylene glycol, in a molar ration of 0:1:0.33:10.5, are heated with 13 g. crotonic anhydride for one hour to 150° C. and for four hours to 180° C. The mass is dissolved in benzene, shaken several times with sodium hydroxide, washed with water and dried in vacuum. Yield: 67 g.

EXAMPLE 13

570 g. of a mixed polymer of tetrahydrofuran and ethylene oxide in a molar radio of 1:1 which has a mean molecular weight in the range of 500 to 20,000 are heated in a $CO_2$ or $N_2$ atmosphere with 46 g. crotonic anhydride for one hour to 150° C., and for one hour to 180° C. The volatile portions are removed subsequently by blowing at 200° C.

EXAMPLE 14

The OH terminal groups of a polyester made from adipic acid, sebacic acid, hexane diol-1,6 and triethylene glycol in molar ratio 18:2:15:6, are treated with crotonic anhydride as described in Example 1.

All of the above polyesters or polyethers can be cured with UV (365 nm) with benzoin alkyl ether or with visible light at 400–450 nm with camphoroquinone and N,N-dimethylamino ethyl methacrylate. The crotonic anhydride can be replaced with methacrylic anhydride and the whole process repeated.

EXAMPLE 15

50 gms of a low molecular weight polyethylene glycol is reacted with 7.5 gms of a liquid urethane elastomer like du Pont's Adiprene L-167 in a suitable solvent at 30° C. The resulting polymer is reacted with crotonic anhydride at 150° C. under nitrogen for two hours and excessive crotonic anhydride removed by a current of nitrogen at 200° C. The product can be mixed with benzoin methyl ether in the range of 0.05% to 1% and cured with UV in the range of 365 nm or mixed with camphoroquinone in the range of 0.05% to 1% and N,N-dimethylamino ethyl methacrylate in the range of 0.05% to 1% and cured with visible light in the region of 400–540 nm.

EXAMPLE 16

Methacrylic anhydride can be substituted for crotinic anhydride in Example 15. The product can be cured by UV or visable light as in Example 15.

EXAMPLE 17

The crotonic or methacrylic anhydrides can be replaced with acrylic anhydride. Acrylic functionally can be cured faster and to a higher degree of cross-linking due to the higher reactivity of the acrylate group over the crotonate or methacrylate. The acrylate is inherently more "toxic" than either the crotonate or methacrylate and that is why the latter are used more often in dentistry. However, one could produce blends of acrylate and methacrylates to achieve a range of photo initiated cures.

EXAMPLE 18

The above polymers can be blended with fillers or reinforcing agents to improve both the stiffness (modulus) and the toughness of the finished product. In addition, the filler reinforcing agent would also increase the viscosity of the impression material to make it more workable. Fillers/reinforcing agents could be added in the range of 30–80% by weight with particle sizes in the range of 0.04 to 15 μm. (micrometers).
The filler includes:
(1) Talc
(2) Calcium Carbonate
(3) Colloidal Silica
(4) Glass
(5) Quartz, etc.

EXAMPLE 19

The viscosity of a polyester impression material was increased by the use of a non-reactive filler. Fifty grams of an elastomeric polyether impression material was mixed with 50 gms talc until the mixture was smooth. Twenty grams of the talc filler polyether was mixed with about two grams of a standard polyether curing agent. Crosslinking occurred in a few minutes at room temperature to give a product with hard rubber properties.

Some suitable filler compositions are as follows:

EXAMPLE 20

The viscosity of a polyether impression material was increased by the use of a non-reactive filler. Fifty grams of an elastomeric polyether impression material was mixed with 50 grams of calcium carbonate until smooth. Twenty grams of the calcium carbonate filled polyether was crosslinked at room temperature with a standard impression material crosslinking agent to give a rubbery product.

EXAMPLE 21

The viscosity of a polyether impression material was increased by the use of a non-reactive filler. Fifty grams of an elastomeric polyether impression material was mixed with 50 gms of a fumed silica like CAB-O-SIL ®. When crosslinked at room temperature, the filled material gives a product with rubbery properties.

EXAMPLE 22

The viscosity of a polyether impression material was increased by adding a quantity of a crosslinking agent, such that the molecular weight is increased by chain extension with little or no crosslinking occurring. Fifty grams of the polyether is reacted with benzene sulfonic acid in the range of 0.005 to 0.1 gm to give a product with properties of a gum elastomer. Complete curing can be accomplished by further addition of the acid.

EXAMPLE 23

50 gms of a low molecular weight polyethylene glycol is reacted with 7.5 gms of a liquid urethane elastomer like du Pont's Adiprene L-167 in a suitable solvent at 30° C. The resulting polymer is reacted with crotonic anhydride at 150° C. under nitrogen for two hours and excessive crotonic anhydride removed by a current of nitrogen at 200° C.

The product was reacted with 10 gm of ethylene imine for seven days at room temperature. The ethylene imine compound was mixed with 0.06 gm of benzene sulfonic acid methylester in the range of 0.05 to 5% to give a crosslinked product.

EXAMPLE 24

A low molecular weight polyethylene glycol is reacted with a low molecular weight carboxy terminated polybutadiene at 150° C. under nitrogen for two hours. 50 gms of the mixture was reacted with 10 gms of ethylene imine at 50° C. The resulting product is reacted with benzene sulfonic acid methylester to give a crosslinked product.

EXAMPLE 25

50 gm-a copolymer of isobutylene and isoprene (5–25% isoprene) with a molecular weight in the range of 10,000 to 250,000 is dissolved in toluene and 8 gms of ethylene imine is added. The mixture is stored at room temperature for five days. 1 gm of the mass obtained by evaporation of the solvent is reacted with 0.06 gm of benzene sulfonic methylester to give a crosslinked product.

EXAMPLE 26

A gum terpolymer of ethylene, propylene and from 1–15% of an unsaturated monomer from 1,4 hexadiene is reacted with ethylene imine. 1 gm of this ethylene imine adduct is mixed with an acid catalyst line benzene sulfonic acid methylester to give a crosslinked elastomer.

Silicone Impression Materials

A silanol terminated poly(dimethylsiloxane) with the structure:

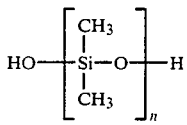

where n = 74.0 10,000
mol. wgt. = 7500–750,000 can be reacted with acryloyl, crotonoyl or methacryloyl chloride to yield materials which can be photochemically cured (crosslinked).

Some examples of suitable photochemically cured silicone impression materials follows:

EXAMPLE 27

100 gms of a silanol terminated poly(dimethyl siloxane) with an average molecular weight of 70,000 is dissolved in 400 ml hexane and 5 gm of acryloyl chloride and a small amount (5 gm) of pyridine (acid acceptor) is added. The mixture is heated at 50° C. for one hour, cooled and filtered. The solvent and unreacted acryloyl chloride are removed under vacuum at room temperature. Benzoin alkyl ether in the range of 0.05% and 1% (based upon weight of product) is mixed with the acrylate capped poly(dimethylsiloxane) product and subjected to ultraviolet light in the region of 365 nm. The mixture is transfored into a transparent rubbery mass.

EXAMPLE 28

The product of Example 27 is mixed with camphoroquinone in the range of 0.05% to 1% N,N-dimethylaminoethyl methacrylate in the range of 0.05% to 1% based on the weight of the polymeric product. When the mixture is exposed to visible light in the range of 400–450 nm, a transparent rubber elastic mass is formed.

EXAMPLE 29

Example 27 is followed except that 5 gm of crotonoyl chloride is added instead of the acryloyl chloride and reacted in a similar fashion. The solvent and excess crotonoyl chloride are removed by a vacuum at 50°–200° C. Addition of benzoin alkyl ether in the range of 0.05% to 1% and subjecting mixture to ultraviolet light in the region of 365 nm gives rubbery product.

EXAMPLE 30

Camphoroquinone in the range of 0.05% to 1% N,N dimethylamino ethyl methacrylate in the range of 0.05% to 1% is added to the product in Example 29. When the mixture is exposed to visible light in the region of 400–450 nm, a crosslinked rubber-like mass is formed.

EXAMPLE 31

Example 27 is followed except that 5 gm of methacryloyl chloride is added instead of acryloyl chloride and reacted in the same way. The solvent and excess methacryloyl chloride are removed under vacuum at 50° C.

Addition of benzoin alkylether in the range of 0.05% to 1% and subjecting the mixture to ultraviolet light in the region of 365 nm gives a crosslinked rubbery product.

EXAMPLE 32

Camphoroquinone and 0.1% N,N dimethylamino ethyl methacrylate is added to the product in Example 31. When the mixture is exposed to visible light in the region of 400–450 nm a crosslinked rubbery product is produced.

EXAMPLE 33

Silanol terminated copolymers of dimethylsiloxane and diphenylsiloxane of the structure

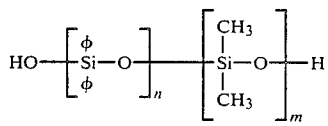

can be substituted for polydimethylsiloxane in Examples 27–34.

EXAMPLE 34

100 gms silanol terminated poly(dimethylsiloxane) is dissolved in hexane and an excess of dichlorodimethylsilane is added and stored at room temperature under dry nitrogen. The excess dichlorodimethylsilane is removed by vacuum at room temperature. 5 gms of acrylic acid is added to the chlorine terminated siloxane and heated at 50° C. for one hour. The excess acrylic acid and hexane are removed under vacuum at 100° C. to give a product with acrylate end groups.

Benzoin alkylether in the range of 0.05% to 1% is mixed with the product and the mixture subjected to UV light in the region of 365 nm. The mixture is transformed into a crosslinked rubbery mass.

EXAMPLE 35

Camphoroquinone in the range of 0.05% to 1% and N,N dimethylamino ethyl methacrylate in the range of 0.05% to 1% are mixed with the product in Example 34 and the mixture exposed to visible light in the region of 400–450 nm to give a crosslinked rubbery mass.

Polysulfide Impression Materials Cured Photochemically

A polysulfide polymer possessing mercaptan end groups with the structure:

when $R = C_2H_2$ etc.
(These are the Thiokol liquid polymers) Molecular Weights 1000–100,000
can be reacted with acryloyl, crotonoyl or methacryloyl chloride to yield polysulfide materials which can be photochemically cured.

Some examples follow.

EXAMPLE 36

100 gms of Thiokol LP-3 (average molecular weight 4000) is dissolved in 400 ml of toluene and 5 gms of acryloyl chloride and a small amount of pyridine (acid acceptor) is added. The mixture is heated at 50° C. for one hour, cooled and filtered. The solvent and unreacted acryloyl chloride are removed under vacuum at 100° C.

Benzoin in alkylether in the range of 0.05% to 1% (based upon weight of polysulfide product) is mixed with the acrylate capped polysulfide and subjected to ultraviolet light in the region of 365 nm. The mixture is transformed into a transparent rubbery product.

EXAMPLE 37

The product of Example 36 is mixed with camphoroquinone in the range of 0.05% to 1% N,N-dimethylamino ethyl methacrylate in the range of 0.05% to 1% based on the weight of the polysulfide. When the mixture is exposed to visible light in the range of 400–450 nm, a transparent rubbery product is produced.

EXAMPLE 38

Substitute crotonoyl chloride for acryloyl chloride in Example 36—cure with both ultraviolet visible light as in Examples 36 and 37.

EXAMPLE 39

Substitute crotonoyl chloride for acryloyl chloride in Example 36. Cure with both ultraviolet and visible light as in Examples 36 and 37.

EXAMPLE 40

In Examples 36–39, vary the molecular weight from 1000 to 100,000—above 100,000 will probably be too viscous to handle.

EXAMPLE 41

100 gm of propylene sulfide is dissolved in 500 ml dry tetrahydrofuran (THF). The solution is chilled to −78° C. under nitrogen with dry ice/acetone. To this mixture is added 6 ml of a 1M sodium naphthalene solution.

After one hour 0.9 ml of ethylene oxide is added to the reaction mixture followed by 1 ml of acetic acid. The mixture is allowed to warm to 50° C., and 5 gms of acryloyl chloride and a small amount of pyridine is added and allowed to react for one hour. The solvent and excess acryloyl chloride are removed by vacuum at 50° C. The product of acrylate capped poly(propylene sulfide) can be cured by ultraviolet and visible light as in Examples 36 and 37.

EXAMPLE 42

Carry out reaction as in Example 41 and terminate with crotonoyl chloride or a methacryloyl chloride instead of acryloyl chloride. (Methacryloyl chloride preferred.) Cure as in Examples 36 and 37.

OPERATION

In use, an elastomeric material formed in accordance with one of the above examples, of desired density and impregnated with any of a variety of known hemostatic agents such as vasoconstrictors or astringents, such as epinephrine or aluminum chloride, or aluminum sulfate or the like, but not limited to, is provided.

This elastomeric material may be packaged in a variety of ways. Thus, it is preferred that where the material is used for obtaining both subgingival and supra-gingival tooth areas, the elastomeric material be packaged in two separate flexible walled containers or rigid containers from which the material may be selectively expelled. The elastomer in each container is preferably differently colored.

Where a tooth impression is to be taken, the gum is pushed back and the elastomer from one of the containers is forced into the space between the gum and subgingival tooth area, and brought up against the tooth. Thereafter, elastomer from the other tube is applied about the supra-gingival tooth surface.

It is preferred that the elastomer be of one of the above described photochemically curable types, and the elastomer is cured by exposing the elastomer to a suitable light source, that may even be from a laser. Since curing does not occur until the light is applied, the dentist may work at a pace suited to obtaining maximum accuracy, without being bound to the cure rate of the elastomer.

Where chemical curing is employed, the elastomer is employed as above. The resulting impression will have a clear line of demarcation between supra and sub-gingival tooth areas, and the need for retracting cords will be eliminated.

The elastomer may also be employed for denture relining by arranging a preferably photochemically curable elastomer between the denture plate and the alveloer ridge. After desired contouring of the elastomer, curing is effected by exposing the elastomer to light.

The above disclosure has been given by way of illustration and elucidation, and not by way of limitation, and it is desired to protect all embodiments of the herein disclosed inventive concept within the scope of the appended claims.

What is claimed is:

1. A method for using a photochemically cured elastomer as an implant comprising the steps of:
   exposing an area for implant;
   applying and positioning a photochemically curable elastomeric material to said exposed area;
   applying sufficient pressure to seat and mold the elastomeric material at the desired position in a desired size and shape; and
   curing the elastomeric material using a light source.

2. A method of relining a denture at chairside comprising the steps of:
   applying a photochemically curable elastomeric material to the denture surface requiring relining;
   positioning the denture in the mouth of the patient with the elastomeric material sandwiched between the denture and the alveolar ridge;
   applying sufficient pressure to the denture to seat the same at a desired position in the mouth of the patient; and
   curing the elastomeric material in or out of the mouth using a light source.

* * * * *